(12) United States Patent
Surti

(10) Patent No.: US 9,339,265 B2
(45) Date of Patent: May 17, 2016

(54) MEDICAL DEVICES, SYSTEMS, AND METHODS FOR USING TISSUE ANCHORS

(75) Inventor: Vihar C. Surti, Winston-Salem, NC (US)

(73) Assignee: Cook Medical Technologies LLC, Bloomington, IN (US)

( * ) Notice: Subject to any disclaimer, the term of this patent is extended or adjusted under 35 U.S.C. 154(b) by 1671 days.

(21) Appl. No.: 12/236,236

(22) Filed: Sep. 23, 2008

(65) Prior Publication Data

US 2009/0082786 A1    Mar. 26, 2009

Related U.S. Application Data

(60) Provisional application No. 60/974,996, filed on Sep. 25, 2007.

(51) Int. Cl.
*A61B 17/04* (2006.01)

(52) U.S. Cl.
CPC ..... *A61B 17/0401* (2013.01); *A61B 2017/0409* (2013.01); *A61B 2017/0417* (2013.01)

(58) Field of Classification Search
CPC ........... A61B 17/0401; A61B 17/0469; A61B 17/0483; A61B 2017/0409; A61B 2017/0488; A61B 2017/0417
USPC ........................... 606/139, 142, 144, 148, 232
See application file for complete search history.

(56) References Cited

U.S. PATENT DOCUMENTS

| | | |
|---|---|---|
| 2,199,025 A | 4/1940 | Conn |
| 3,556,079 A | 1/1971 | Omizo |
| 4,235,238 A | 11/1980 | Ogiu et al. |
| 5,085,661 A * | 2/1992 | Moss ............................ 606/139 |
| 5,123,914 A | 6/1992 | Cope |
| 5,203,787 A | 4/1993 | Noblitt et al. |
| 5,333,624 A | 8/1994 | Tovey |
| 5,366,480 A | 11/1994 | Corriveau et al. |
| 5,417,691 A | 5/1995 | Hayhurst |
| 5,520,700 A | 5/1996 | Beyar et al. |
| 5,527,343 A | 6/1996 | Bonutti |
| 5,554,183 A | 9/1996 | Nazari |
| 5,643,293 A * | 7/1997 | Kogasaka et al. ............. 606/148 |
| 5,662,683 A | 9/1997 | Kay |
| 5,690,656 A | 11/1997 | Cope et al. |
| 5,728,124 A | 3/1998 | Cockburn et al. |
| 5,797,928 A * | 8/1998 | Kogasaka ..................... 606/144 |
| 5,807,304 A | 9/1998 | Cockburn |
| 5,810,848 A | 9/1998 | Hayhurst |

(Continued)

FOREIGN PATENT DOCUMENTS

| | | |
|---|---|---|
| WO | WO01/58363 | 8/2001 |
| WO | WO2006/109377 | 10/2006 |

OTHER PUBLICATIONS

WO Publication with International Search Report for PCT/US2008/077382; 27 pages.

(Continued)

*Primary Examiner* — Alexander Orkin
(74) *Attorney, Agent, or Firm* — Brinks Gilson & Lione

(57) ABSTRACT

Medical devices, systems and related methods for delivering a tissue anchor. The medical devices generally comprise a needle and a sheath that assist in retaining the tissue anchor at the distal end of the need during manipulation of the medical device. The medical systems include one or more tissue anchors in conjunction with one of the medical devices.

12 Claims, 3 Drawing Sheets

(56) References Cited

U.S. PATENT DOCUMENTS

| | | |
|---|---|---|
| 5,865,791 A | 2/1999 | Whayne et al. |
| 5,891,159 A | 4/1999 | Sherman et al. |
| 5,908,428 A | 6/1999 | Scirica et al. |
| 5,931,844 A * | 8/1999 | Thompson et al. ............ 606/144 |
| 5,968,078 A | 10/1999 | Grotz |
| 6,053,871 A | 4/2000 | Cockburn |
| 6,110,183 A | 8/2000 | Cope |
| RE36,974 E | 11/2000 | Bonutti |
| 6,290,674 B1 | 9/2001 | Roue et al. |
| 6,328,727 B1 | 12/2001 | Frazier et al. |
| 6,358,197 B1 | 3/2002 | Silverman et al. |
| 6,419,669 B1 | 7/2002 | Frazier et al. |
| 6,423,087 B1 | 7/2002 | Sawada |
| 6,425,887 B1 | 7/2002 | McGuckin et al. |
| 6,482,178 B1 | 11/2002 | Andrews et al. |
| 6,491,707 B2 | 12/2002 | Makower et al. |
| 6,551,333 B2 | 4/2003 | Kuhns et al. |
| 6,572,629 B2 | 6/2003 | Kalloo et al. |
| 6,592,559 B1 | 7/2003 | Pakter et al. |
| 6,626,919 B1 * | 9/2003 | Swanstrom .................... 606/153 |
| 6,641,557 B1 | 11/2003 | Frazier et al. |
| 6,699,263 B2 | 3/2004 | Cope |
| 6,712,804 B2 | 3/2004 | Roue et al. |
| 6,746,472 B2 | 6/2004 | Frazier et al. |
| 6,966,916 B2 | 11/2005 | Kumar |
| 7,025,756 B2 | 4/2006 | Frazier et al. |
| 7,056,325 B1 | 6/2006 | Makower et al. |
| 7,087,073 B2 | 8/2006 | Bonutti |
| 7,115,110 B2 | 10/2006 | Frazier et al. |
| 7,217,279 B2 | 5/2007 | Reese |
| 7,326,221 B2 | 2/2008 | Sakamoto |
| 7,326,231 B2 | 2/2008 | Phillips et al. |
| 7,390,329 B2 | 6/2008 | Westra et al. |
| 7,416,554 B2 | 8/2008 | Lam et al. |
| 7,481,826 B2 | 1/2009 | Cichocki, Jr. |
| 7,494,496 B2 | 2/2009 | Swain et al. |
| 7,601,159 B2 | 10/2009 | Ewers et al. |
| 7,618,426 B2 | 11/2009 | Ewers et al. |
| 7,621,925 B2 | 11/2009 | Saadat et al. |
| 7,622,068 B2 | 11/2009 | Li et al. |
| 7,641,836 B2 | 1/2010 | Li et al. |
| 7,695,493 B2 | 4/2010 | Saadat et al. |
| 7,704,264 B2 | 4/2010 | Ewers et al. |
| 2003/0208209 A1 | 11/2003 | Gambale et al. |
| 2004/0147941 A1 | 7/2004 | Takemoto et al. |
| 2004/0153074 A1 | 8/2004 | Bojarski et al. |
| 2004/0220596 A1 | 11/2004 | Frazier et al. |
| 2005/0033363 A1 * | 2/2005 | Bojarski et al. ............... 606/228 |
| 2005/0143762 A1 | 6/2005 | Paraschac et al. |
| 2005/0197594 A1 | 9/2005 | Burbank et al. |
| 2005/0240201 A1 | 10/2005 | Yeung |
| 2005/0240226 A1 * | 10/2005 | Foerster et al. ............... 606/232 |
| 2005/0251166 A1 | 11/2005 | Vaughan et al. |
| 2005/0251206 A1 * | 11/2005 | Maahs et al. .................. 606/232 |
| 2005/0277957 A1 | 12/2005 | Kuhns et al. |
| 2005/0283193 A1 * | 12/2005 | Tullberg et al. ............... 606/232 |
| 2006/0002852 A1 | 1/2006 | Saltzman et al. |
| 2006/0004409 A1 | 1/2006 | Nobis et al. |
| 2006/0004410 A1 | 1/2006 | Nobis et al. |
| 2006/0015006 A1 | 1/2006 | Laurence et al. |
| 2006/0020274 A1 | 1/2006 | Ewers et al. |
| 2006/0135989 A1 | 6/2006 | Carley et al. |
| 2006/0190016 A1 | 8/2006 | Onuki et al. |
| 2006/0206063 A1 | 9/2006 | Kagan et al. |
| 2006/0207608 A1 | 9/2006 | Hirotsuka et al. |
| 2006/0217762 A1 | 9/2006 | Maahs et al. |
| 2006/0235447 A1 | 10/2006 | Walshe |
| 2006/0237022 A1 | 10/2006 | Chen et al. |
| 2006/0241691 A1 | 10/2006 | Wilk |
| 2006/0265010 A1 | 11/2006 | Paraschac et al. |
| 2007/0060929 A1 * | 3/2007 | Onishi et al. .................. 606/139 |
| 2007/0093858 A1 | 4/2007 | Gambale et al. |
| 2007/0100375 A1 | 5/2007 | Mikkaichi et al. |
| 2007/0162052 A1 | 7/2007 | Hashimoto et al. |
| 2007/0191886 A1 | 8/2007 | Dejima et al. |
| 2007/0208360 A1 | 9/2007 | Demarais et al. |
| 2007/0213702 A1 | 9/2007 | Kogasaka et al. |
| 2007/0270752 A1 | 11/2007 | LaBombard |
| 2007/0270889 A1 | 11/2007 | Conlon et al. |
| 2007/0276424 A1 | 11/2007 | Mikkaichi et al. |
| 2008/0065157 A1 | 3/2008 | Crombie et al. |
| 2008/0114398 A1 | 5/2008 | Phillips et al. |
| 2008/0132948 A1 | 6/2008 | Surti et al. |
| 2008/0154290 A1 | 6/2008 | Golden et al. |
| 2008/0172088 A1 | 7/2008 | Smith et al. |
| 2008/0185752 A1 | 8/2008 | Cerwin et al. |
| 2008/0200930 A1 | 8/2008 | Saadat et al. |
| 2008/0208214 A1 | 8/2008 | Sato et al. |
| 2008/0208218 A1 | 8/2008 | Shiono |
| 2008/0208219 A1 | 8/2008 | Suzuki |
| 2008/0208220 A1 | 8/2008 | Shiono et al. |
| 2008/0208251 A1 | 8/2008 | Weadock et al. |
| 2008/0228202 A1 | 9/2008 | Cropper et al. |
| 2008/0228203 A1 | 9/2008 | Bell et al. |
| 2008/0243148 A1 | 10/2008 | Mikkaichi et al. |
| 2008/0255422 A1 | 10/2008 | Kondoh et al. |
| 2008/0255427 A1 | 10/2008 | Satake et al. |
| 2008/0269566 A1 | 10/2008 | Measamer |
| 2008/0296344 A1 | 12/2008 | Cropper et al. |
| 2008/0300627 A1 | 12/2008 | Measamer et al. |
| 2008/0319257 A1 | 12/2008 | Sato et al. |
| 2009/0005800 A1 | 1/2009 | Franer et al. |
| 2009/0018602 A1 | 1/2009 | Mitelberg et al. |
| 2009/0069847 A1 | 3/2009 | Hashiba et al. |
| 2009/0076527 A1 | 3/2009 | Miyamoto et al. |
| 2009/0088780 A1 | 4/2009 | Shiono et al. |
| 2009/0125039 A1 | 5/2009 | Mikkaichi et al. |
| 2009/0149714 A1 | 6/2009 | Bonadio |
| 2009/0204147 A1 | 8/2009 | Rahmani |
| 2009/0281559 A1 | 11/2009 | Swain et al. |
| 2009/0299406 A1 | 12/2009 | Swain et al. |
| 2009/0326561 A1 | 12/2009 | Carroll, II et al. |
| 2009/0326578 A1 | 12/2009 | Ewers et al. |
| 2010/0010457 A1 | 1/2010 | Ewers et al. |
| 2010/0042115 A1 | 2/2010 | Saadar et al. |
| 2010/0042144 A1 | 2/2010 | Bennett |
| 2010/0048990 A1 | 2/2010 | Bakos |
| 2010/0056862 A1 | 3/2010 | Bakos |
| 2010/0076462 A1 | 3/2010 | Bakos et al. |
| 2010/0076488 A1 | 3/2010 | Spivey et al. |
| 2010/0094341 A1 | 4/2010 | Raju |
| 2010/0106166 A1 | 4/2010 | Cropper et al. |
| 2010/0113873 A1 | 5/2010 | Suzuki et al. |

OTHER PUBLICATIONS

PCT Written Opinion of the International Searching Authority for PCT/US2008/077382; 7 pages.

PCT Preliminary Report on Patentability for PCT/US2008/077382; 13 pages.

Letter and Amendments Under Article 34 for PCT/US2008/077382; 9 pages.

Bergström et al., "Early clinical experience with a new flexible endoscopic suturing method for natural orifice transluminal endoscopic surgery and intraluminal endosurgery (with videos)." *J Gastrointestinal Endoscopy*, 2008, vol. 67, No. 3, pp. 528-533.

Desilets et al., "Loop-anchor purse-string versus endoscopic clips for gastric closure: a natural orifice transluminal endoscopic surgery comparison study using burst pressures." *J Gastrointestinal Endoscopy*, 2009, vol. 70, No. 6, pp. 1225-1230.

Dray et al., "Air and fluid leak tests after NOTES procedures: a pilot study in a live porcine model (with videos)." *J Gastrointestinal Endoscopy*, 2008, vol. 68, No. 3, pp. 513-519.

Fritscher-Ravens, "Transgastric endoscopy—a new fashion, a new excitement!" *J Endoscopy 2007*; vol. 39, pp. 161-167.

Sclabas et al., "Endoluminal Methods for Gastrotomy Closure in Natural Orifice TransEnteric Surgery (NOTES)." *J Surgical Innovation*, Mar. 2006, vol. 13, No. 1, pp. 23-30.

Sporn et al., "Endoscopic colostomy closure after full thickness excision: comparison of T fastener with multiclip applier." *J Endoscopy* 2008, vol. 40, pp. 589-594.

(56) References Cited

OTHER PUBLICATIONS

Sporn et al., "Endoscopic colostomy closure for natural orifice transluminal endoscopic surgery using a T-fastener prototype in comparison to conventional suture closure." *J Gastrointestinal Endoscopy*, 2008, vol. 68, No. 4, pp. 724-730.

Voermans et al., "In vitro comparison and evaluation of seven gastric closure modalities for natural orifice transluminal endoscopic surgery (NOTES)." *J Endoscopy 2008*, vol. 40, pp. 595-601.

\* cited by examiner

मेडिकल DEVICES, SYSTEMS, AND
METHODS FOR USING TISSUE ANCHORS

CROSS-REFERENCE TO RELATED APPLICATIONS

This application claims the benefit of U.S. Provisional Application Ser. No. 60/974,996 filed on Sep. 25, 2007, entitled "MEDICAL DEVICES, SYSTEMS, AND METHODS FOR USING TISSUE ANCHORS"

FIELD OF THE INVENTION

The present invention relates generally to medical devices for placing tissue anchors in bodily walls, such as for closing perforations in tissue.

BACKGROUND OF THE INVENTION

Perforations in bodily walls may be naturally occurring, or formed intentionally or unintentionally. In order to permanently close these perforations and allow the tissue to properly heal, numerous medical devices and methods have been developed employing sutures, adhesives, clips, staples and the like. One class of such devices is commonly referred to as tissue anchors, T-anchors or visceral anchors. Exemplary tissue anchors are disclosed in U.S. Pat. No. 5,123,914 and U.S. application Ser. No. 11/946,565, the entire contents of which are incorporated by reference herein.

Tissue anchors typically include a crossbar or some anchoring member connected to suture. The anchoring member and suture may take many forms, but generally a needle is used to pierce tissue and deliver the anchoring member on one side of the tissue, leaving the suture extending back to the other side of the tissue. The sutures of one or more tissue anchors are collected and connected together, such as through tying the sutures together. A significant level of skill and coordination is required by the medical professional to tie such sutures together, especially when the tissue site is difficult to access within the body, such as in endoscopic or laparoscopic procedures. Suture locks may also be employed to help collect and connect the sutures together, and exemplary suture locks are disclosed in U.S. application Ser. Nos. 11/946,565 and 12/191,001, the entire contents of which are incorporated by reference herein.

BRIEF SUMMARY OF THE INVENTION

The present invention provides medical devices, systems and related methods for delivering a tissue anchor. One embodiment of such a medical device, constructed in accordance with the teachings of the present invention, generally comprises a needle and a sheath that assist in retaining the tissue anchor at the distal end of the needle during manipulation of the medical device. The needle has a needle lumen sized to slidably receive the tissue anchor. The sheath has a sheath lumen sized to slidably receive the needle. A distal end of the sheath defines a sheath slot sized to receive the suture therein.

According to more detailed aspects of the medical devices, the sheath frictionally engages the suture within the sheath slot. The slot preferably has a width less than or equal to a width of the suture. The slot extends completely through the sheath and is open at one end. The slot may take many forms, and may be formed as a slit having edges which engage each other when there is no suture within the slot. A distal end of the needle preferably defines a needle slot sized to receive the suture of the tissue anchor. The needle slot and sheath slot can be radially mis-aligned to frictionally engage the suture and retain the tissue anchor at the distal end of the device.

The medical devices are generally operable between a delivery configuration and a deployed configuration. The needle is substantially contained within the sheath lumen in the delivery configuration, and the needle projects beyond the distal end of the sheath in the deployed configuration. The suture slides within the sheath slot between the delivery and deployed configurations. The sheath slot may be sized such that the sheath continues to frictionally engage the suture in the deployed configuration, or such that the sheath does not frictionally engage the suture in the deployed configuration. The medical device, together with one or a plurality of tissue anchors, defines a medical system in accordance with the teachings of the present invention.

A method of delivering a tissue anchor is also provided in accordance with the teachings of the present invention. A medical system, such as one of the systems described above, is provided. The medical system is delivered to a position proximate the tissue, preferably in conjunction with an endoscope. The needle is deployed by translating the needle relative to the sheath. The tissue anchor is deployed by translating the tissue anchor relative to the needle such that the tissue anchor exits the needle lumen. The sheath frictionally engages the suture within the sheath slot during the step of delivering the medical system. The suture may disengage the sheath during the step of deploying the needle, or the suture may disengaged the sheath during the step of deploying the tissue anchor. When the medical system includes a plurality of tissue anchors serially aligned within the needle lumen, the step of deploying the tissue anchor is repeated for at least a portion of the plurality of tissue anchors.

BRIEF DESCRIPTION OF THE DRAWINGS

The accompanying drawings incorporated in and forming a part of the specification illustrate several aspects of the present invention, and together with the description serve to explain the principles of the invention. In the drawings.

DETAILED DESCRIPTION OF THE INVENTION

Figure 1:
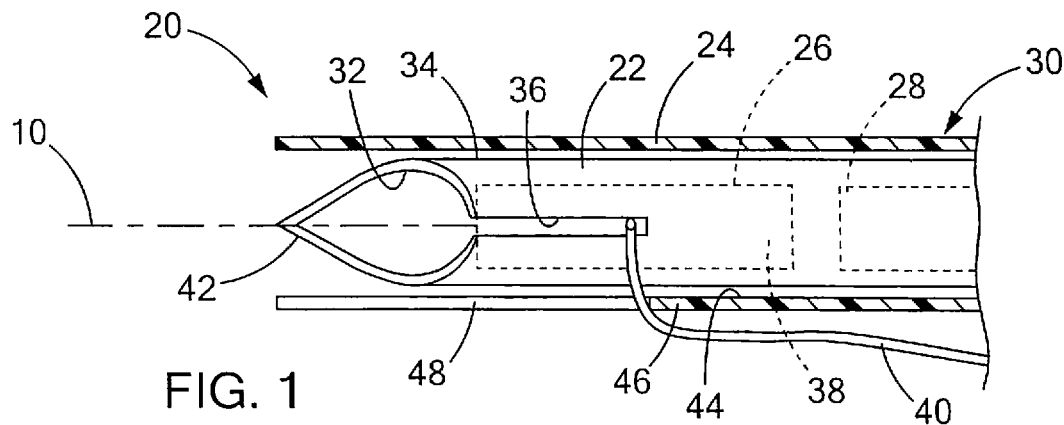
FIG. 1 is a plan view, partially in cross-section, of a medical device and system constructed in accordance with the teachings of the present invention.

Turning now to the figures, FIG. 1 depicts a medical device 20 constructed in accordance with the teachings of the present invention. The medical device 20 generally comprises a needle 22 and a sheath 24. The medical device 20 is designed for delivering a tissue anchor 26, and the device 20 preferably also includes a pusher 28 extending through the needle 22 for expelling the anchor 26 therefrom.

The medical device 20 and tissue anchor 26 together form a medical system 30. That is, the medical device 20 may be utilized with a number of different tissue anchors, and therefore the medical device 20 may be provided separately such that the medical professional may utilize tissue anchors of his or her own choosing. At the same time, the medical device 20 may be also provided with tissue anchors 26 "pre-loaded", thereby forming a medical system 30 in accordance with the teachings of the present invention.

The needle 22 defines a needle lumen 32 and a longitudinal axis 10 of the medical device 20. The needle 22 is preferably constructed of a metal or alloy such as stainless steel or nitinol, although other metals, alloys and plastics can be used for the needle 22, as is known in the art. The needle lumen 32 is sized to slidably receive the tissue anchor 26 therein. In particular, the tissue anchor 26 generally comprises an anchoring member 38 and a suture 40 attached thereto, and the anchoring member 38 is received within the needle lumen 32 along with a portion of the suture 40. A distal end 34 of the needle 22 also defines a needle slot 36 that is longitudinally extending and opens longitudinally at the distal end 34 of the needle 22. The slot 36 is sized to receive the suture 40 therein. It will be recognized that the needle 22 may not include the slot 36, although it is preferable to keep the suture 40 safe from the sharp distal tip 42 of the needle 22 through provision of the slot 36.

The sheath 24 defines a sheath lumen 44 which is sized to slidably receive the needle 22 therein. The sheath 24 is preferably formed of a plastic such as polytetrafluorethylene (PTFE), expanded polytetrafluoroethylene (EPTFE), polyethylene ether ketone (PEEK), polyvinylchloride (PVC), polycarbonate (PC), polyamide including nylon, polyimide, polyurethane, polyethylene (high, medium or low density), or elastomers such as Santoprene®, including multi-layer or single layer constructions with or without reinforcement wires, coils or filaments. The needle 22, sheath 24 and pusher 28 are preferably elongated structures that are flexible, allowing navigation within a patient's body such as during endoscopic or laparoscopic procedures. As such, a suitable handle or control mechanism will be connected to the proximal ends of the needle 22, sheath 24 and pusher 28 for relative translation of these components by the medical professional, as is known in the art. At the same time, the medical devices 20 and systems 30 are also applicable to other tissue anchor placement devices that may be used in open surgery, on external wounds, or that otherwise do no require an elongated medical device to access the targeted tissue.

Applicants have found that it can often be difficult to retain a tissue anchor within the distal end of a needle, and that the anchor can often be displaced from the needle during manipulation of the needle, e.g. during preparation for a procedure. Accordingly, a distal end 46 of the sheath 24 defines a sheath slot 48 which is sized to receive the suture 40 therein. The sheath slot 48 is preferably sized and structured to frictionally engage the suture 40. As best seen in the side view of FIG. 3, the sheath slot 48 preferably has a width W that is sized to be less than or equal to a width of the suture 40. In this manner, the sheath 24 frictionally engages the suture 40 to retain the tissue anchor 26 within the needle lumen 32. In one preferred construction, the sheath 24 has an outer diameter of about 0.068 inches, an inner diameter of about 0.044 inches, and the slot has a longitudinal length of about 8 mm to about 16 mm, and most preferably about 12 mm.

Figure 2:
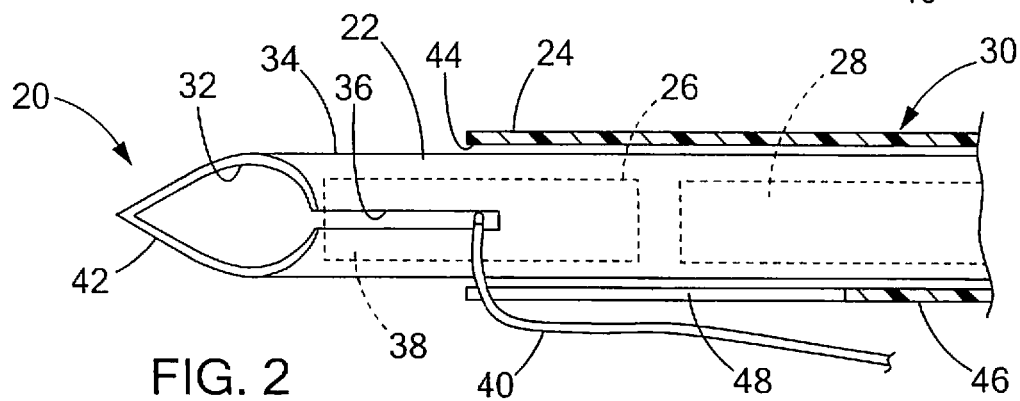
FIG. 2 is a plan view similar to FIG. 1, but showing a deployed configuration of the medical device and system.
Figure 3:
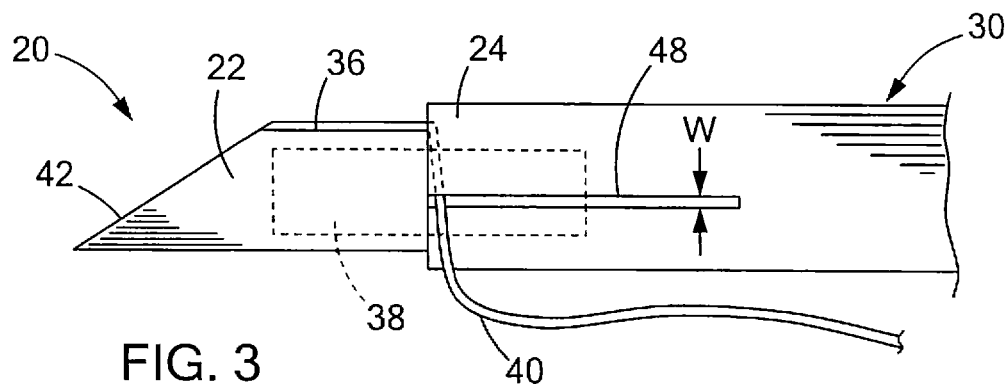
FIG. 3 is a side view of the medical device and system depicted in FIGS. 1 and 2.

It will also be recognized by those skilled in the art that the width W of the sheath slot 38 can also be larger than a width of the suture 40. For example, the needle slot 36 and sheath slot 48 may be radially misaligned (e.g. they may be rotated relative to one another, as illustrated in FIGS. 2 and 3). The suture 40 follows a somewhat tortuous path from within the needle lumen 32, through the needle slot 36, along the exterior of the needle 22 within the sheath lumen 44, and finally through the sheath slot 48. Accordingly, this tortuous path can be sufficient to retain the tissue anchor 26 within the needle lumen 32, through frictional engagement of the suture 40 between the exterior surface of the needle 22 and the interior surface of the sheath 24. Similarly, the sheath slot 48 may extend longitudinally along a curved, S-shaped, zig-zag, or other non-linear path to facilitate retaining the suture 40 and anchor 26. The width W can also vary along the length of the slot 38, and additional structures can mechanically retain the suture within the slot, such as the projections described below with reference to FIG. 8.

The medical device 20 is operable between at least a delivery configuration, depicted in FIG. 1, and deployed configuration, depicted in FIG. 2. In the delivery configuration, the needle 22 is substantially contained within the sheath lumen 44 so as to protect bodily structures from the sharp distal tip 42 of the needle 22 during introduction of the medical device 20. In the delivery configuration, the sheath slot 48 overlaps the needle slot 36 in the longitudinal direction, and the suture 40 extends through the two slots 46, 48. Through the provision of the sheath slot 48 in the sheath 24, the tissue anchor 26 remains securely contained within the needle 22 during introduction.

In the deployed configuration, the needle 22 is translated relative to the sheath 24 such that the needle 22 projects beyond the distal end 46 of the sheath 24. During this relative translation, the tissue anchor 26 is urged distally along with the needle 22 (i.e. urged to the left on the page in the figures) by virtue of the suture 40 engaging the slot 36 in the needle 22, and/or through the simultaneous translation of the pusher 28. The suture 40 also slides distally within the sheath slot 48 formed within the sheath 24. Preferably, the sheath slot 48 is sized and structured such that even in the deployed configuration, the suture 40 still remains within a portion of the sheath slot 48 to assure that the tissue anchor 26 does not inadvertently exit the needle lumen 32.

Figure 4:
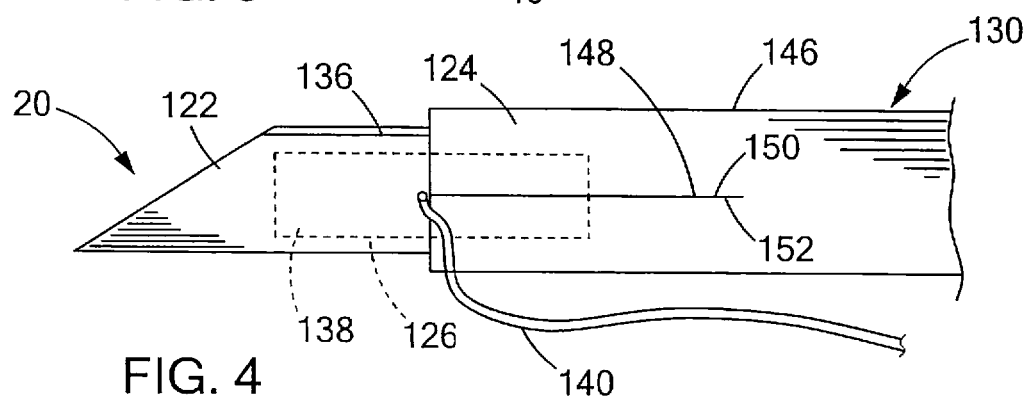
FIG. 4 is a side view similar to FIG. 3, but showing an alternate embodiment of the medical device and system depicted in FIGS. 1-3.

FIG. 4 depicts an alternate embodiment of a medical device 120 and medical system 130. As in the previous embodiment, a needle 122 defines a needle slot 136 and contains a tissue anchor 126 having an anchoring member 138 and a suture 140. In this embodiment, the sheath 124 defines a sheath slot 148 that is formed as a slit. The slit is generally formed by simply cutting or tearing the distal end 146 of the sheath 124. Accordingly, the side edges 150, 152 of the slot 148 may remain in contact when there is no suture 140 extending therethrough, but may separate to frictionally engage a suture 140 extending through the sheath slit 148. Accordingly, it will be recognized by those skilled in the art that the term "slot" as used herein, may include many forms, including slits, notches, channels, holes or passageways, with side edges that may overlap, contact each other, or be spaced apart. The embodiment of FIG. 4 also illustrates that, in the deployed configuration of the medical device 120, the sheath slot 148 may be sized and structured such that the suture 140 traverses along and exits the slot 148 when the needle 122 has reached its deployed position.

Figure 8:
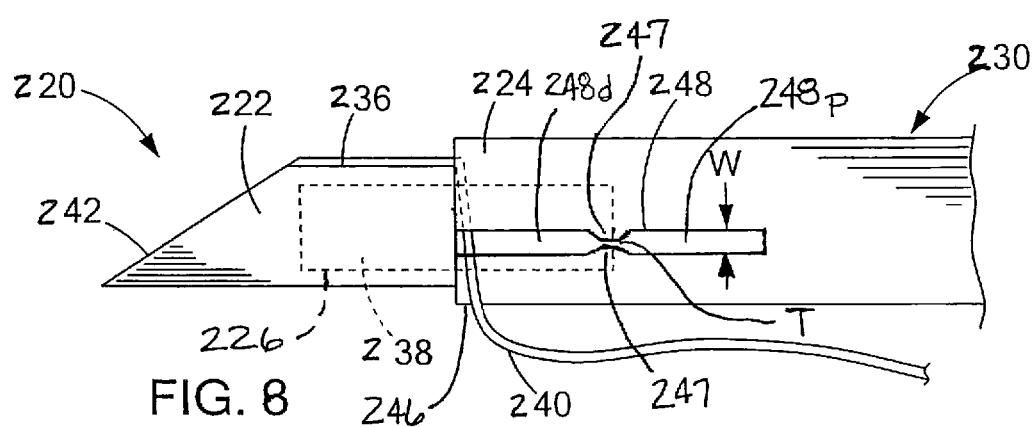
FIG. 8 is a plan view, partially in cross-section, of another embodiment of a medical device and system constructed in accordance with the teachings of the present invention.

FIG. 8 depicts another alternate embodiment of a medical device 220 and medical system 230 which mechanically retains the suture 240 of the tissue anchor 226. As in the previous embodiment, a needle 222 defines a needle slot 236 and slidably receives the tissue anchor 226 having an anchoring member 238 and suture 240. In this embodiment, the sheath 224 defines a sheath slot 248 that has a width W that is about equal to or greater than a diameter/width of the suture 240. Additionally, the slot 248 includes one or more projections 247 extending into the open area of the slot 248 to define a throat T having a reduced width. Two opposing projections 247 having a semi-annular shape have been shown in FIG. 8, although the projections may take any desired shape, e.g. a ramp shape would make proximal translation of the suture 240 past the throat T difficult while at the same time facilitating distal translation of the suture 240.

In the embodiment of FIG. 8, the width of the throat T is preferably about equal to or less than the width W of the remainder of the slot 248. As such, the throat T divides the slot 248 into a proximal slot portion 248p and a distal slot portion 248d. To retain the tissue anchor 226 and its suture 240 to the sheath 224, the suture 240 initially is loaded through the proximal slot portion 248p. The throat T of the slot 248 assists in maintaining the suture 240 in the proximal slot portion 248p. That is, in the delivery configuration, the suture 240 extends through the proximal slot portion 248p to securely retained the tissue anchor 226 within the needle 222 during introduction.

The suture 240 may be moved through the throat T in various ways. For example, in the deployed configuration of the needle 222 (shown in FIG. 8), the needle 222 is moved to project beyond the distal end 246 of the sheath 224, which also urges the tissue anchor 226 distally relative to the sheath 224 and slot 248 and into the distal slot portion 248d. The sheath 222 and its projections 247 have sufficient flexibility and resiliency to widen the throat T (the suture 240 may also be compressed) to permit the suture 240 to pass into the distal slot portion 248d. In the deployed configuration, the suture 240 may still remain within the distal slot portion 248d, or may be located beyond the distal end 246 of the sheath 224. At the same time or alternatively, the tissue anchor 226 may urged distally via translation of the pusher 28 (shown FIG. 2) to move the suture 240 from the proximal slot portion 248p to the distal slot portion 248d. It will be recognized that various types of structures may be used, such as the projections 247, to mechanically retain the tissue anchor 226.

A method for delivering a tissue anchor through tissue 12 will now be described with reference to FIGS. 1, 5 and 6. The method includes providing a medical system having a tissue anchor, a needle and a sheath, such as the medical system 30 depicted in FIGS. 1-3. The medical system 30 is delivered to a position proximate tissue 12 that has been targeted for placement of a tissue anchor 26. Preferably, an endoscope 14 is employed and the medical system 30 is translated through the working channel 16 of the endoscope 14. The endoscope 14 also preferably includes a visualization system 18 for assisting in locating the tissue 12, identifying a target site for deployment of the tissue anchor 26, and monitoring operation of the medical device 20 and system 30. It will be recognized that the medical device 20 and system 30 may be delivered to a position proximate the tissue 12 without the use of an endoscope 14, and likewise other visualization techniques may be employed including catheter-based fiber optic systems, fluoroscopy, ultrasound or the like. For example, the needle 22 can have markings designed for viewing under fluoroscopy, and the distal end of the needle 22 can have a surface of enhanced ultrasonic reflectivity, such by being roughened, having dimples or other incongruities, or having embedded particles. In the latter case, the endoscope 14 may comprise an ultrasound-enabled endoscope permitting placement of the tissue anchor 26 under EUS guidance, thereby facilitating placement within or between layers of tissue (e.g. within the submucosal layer) or preventing puncture of other organs or tissue behind the selected bodily wall.

Figure 5:
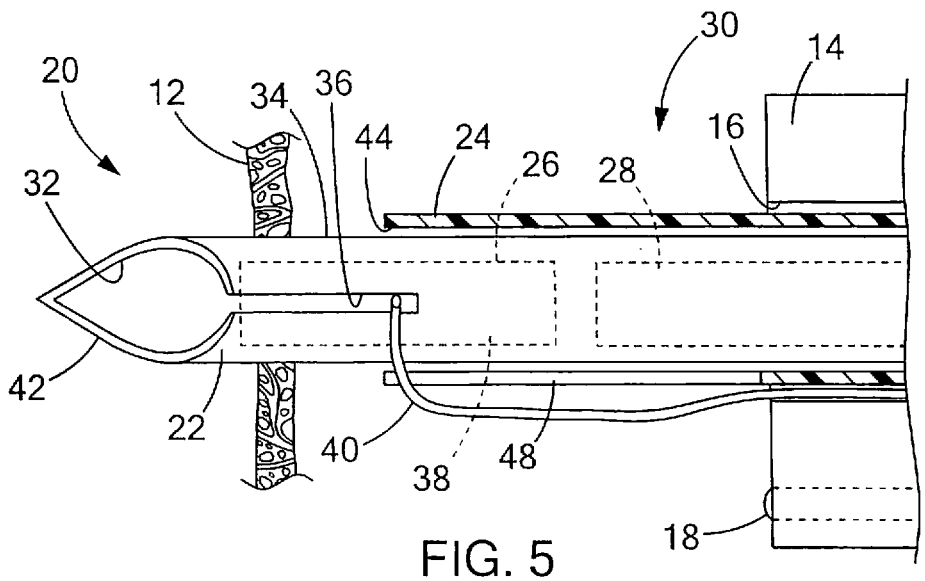
FIGS. 5 and 6 depict steps in a method for using the medical device and system depicted in FIGS. 1-3.

The medical device 20 and system 30 are operated into their deployed configuration, as shown in FIG. 5. In particular, the needle 22 is deployed by translating the needle 22 relative to the sheath 24. Here, the needle 22 can simply be advanced relative to the sheath 24 until it pierces the tissue 12, or the needle 22 may be advanced such that the medical device 20 takes its deployed configuration as shown in FIG. 2, and then the entire medical device 20 and system 30 are together advanced forward through the tissue 12. Likewise, the endoscope 14 may also be advanced along with medical device 20 and system 30.

Figure 6:
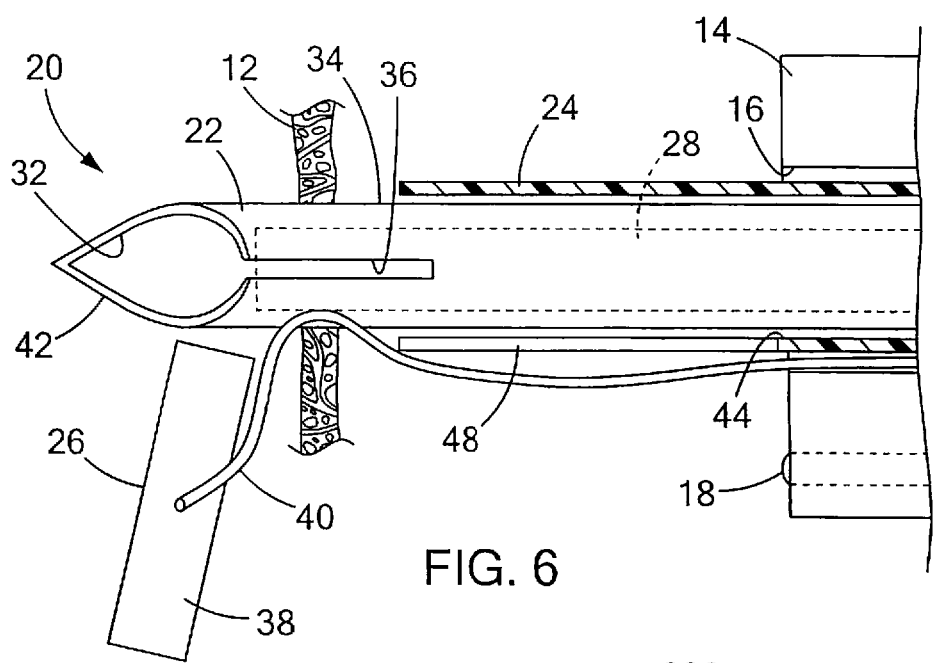

As shown in FIG. 6, the tissue anchor 26 has been deployed by translating the tissue anchor 26 relative to the needle 22 such that the anchor 26 exits the needle lumen 32. Generally, the pusher 28 is advanced distally to press upon the anchoring member 38 of the tissue anchor 26 and move it distally until it exits the needle lumen 32. It will be recognized by those skilled in the art that other structures or mechanisms can replace the pusher 28 and effectively advance the tissue anchor 26. As the anchoring member 38 is translated distally, the suture 40 of the tissue anchor 26 is freed from the sheath slot 48, and likewise moves along the needle slot 36 until the entire anchor 26 is freed from the medical device 20. As previously discussed, depending upon the size and shape of the sheath slot 48, the suture 40 may disengage the sheath 24 during either the step of deploying the needle 22, or during the step of deploying the tissue anchor 26.

Upon deployment of the tissue anchor 26, the needle 22 and/or the sheath 24 may be retracted through the working channel 16 of the endoscope 14 such that the medical device 20 is withdrawn from the tissue 12 and removed from the body. The medical device 20, and in particular the needle 22 may be reloaded with another tissue anchor 26, or the procedure may end. If reloaded with another tissue anchor 26, the above-described steps may be repeated to place additional tissue anchors 26 through the tissue 12.

Figure 7:
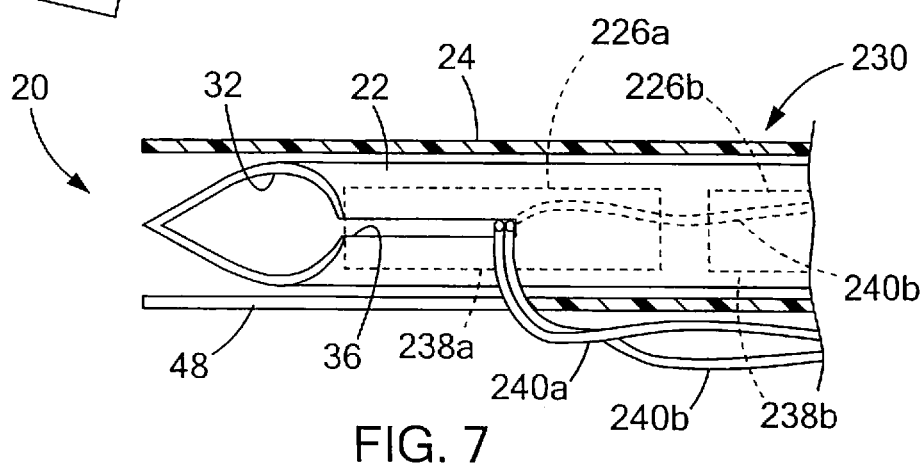
FIG. 7 is a plan view, partially in cross-section, depicting another alternate embodiment of the medical device and system depicted in FIGS. 1-3.

FIG. 7 depicts another embodiment of the medical device 220 and system 230 constructed in accordance with the teachings of the present invention. In this embodiment, the medical device 20 is identical to the medical device previously described with reference to FIGS. 1-3 and generally includes a needle 22 and sheath 24. The needle defines a needle slot 36 while the sheath 24 defines a sheath slot 48. In this embodiment, however, the medical system 230 includes a plurality of tissue anchors 226a, 226b, etc. As shown, the anchors 226a, 226b include anchoring members 238a and 238b connected to sutures 240a and 240b, respectively. The sutures 240a and 240b extend through the needle lumen 32 and through the needle slot 36. Then, the sutures 240a, 240b extend through the sheath slot 48, which frictionally retains them therein.

Accordingly, it will be recognized that a large number of tissue anchors may be employed within the medical device 20, and the longitudinal length of needle slot 36 and sheath slot 48 can be sized to accommodate any number of sutures. In this manner, the medical device 20 need not be withdrawn to be reloaded. The method may therefore include withdrawing the needle 22 from the tissue 12 by translating the needle 22 proximally, and then repeating the steps of translating the needle 22 through the tissue 12 and deploying a tissue anchor therethrough. As shown in FIG. 7, the anchoring members 238a and 238b are shown aligned within the needle lumen 32 such that the pusher 28 may be used to press on the proximal—most anchoring member 38, which will in turn transmit force through all of the anchoring members to cause transmission of the distal-most tissue anchor out of the needle 22.

The foregoing description of various embodiments of the invention has been presented for purposes of illustration and description. It is not intended to be exhaustive or to limit the invention to the precise embodiments disclosed. Numerous modifications or variations are possible in light of the above teachings. The embodiments discussed were chosen and described to provide the best illustration of the principles of the invention and its practical application to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally, and equitably entitled.

The invention claimed is:

1. A medical system comprising:
    a tissue anchor having an anchoring member connected to a suture;
    a needle having a length and a needle lumen slidably receiving the tissue anchor wherein a distal end of the needle defines a needle slot sized to receive the suture of the tissue anchor, the needle and needle lumen defining a longitudinal axis; and
    a flexible sheath having a sheath lumen sized to slidably receive the needle, the sheath extending along the length of the needle, a distal end of the sheath defining a sheath slot sized to receive the suture therein, the sheath slot having a proximal end and a distal end, the sheath slot extending through the distal end of the sheath and sized along its entire length to frictionally engage the suture within the sheath slot,
    wherein the medical system is operable between a delivery configuration and a deployed configuration, the needle being substantially contained within the sheath lumen in the delivery configuration, the needle projecting beyond the distal end of the sheath in the deployed configuration, and wherein the sheath frictionally engages the suture within the sheath slot in the delivery configuration.

2. The medical device of claim 1, wherein the sheath slot has a width less than or equal to a width of the suture.

3. The medical device of claim 1, wherein the slot is formed as a slit having edges which engage each other when there is no suture within the sheath slot.

4. The medical device of claim 1, wherein the needle slot and sheath slot are circumferentially mis-aligned.

5. The medical device of claim 1, wherein the sheath slot overlaps the needle slot.

6. The medical system of claim 1, wherein the suture is slidable within the slot between the delivery and deployed configurations.

7. The medical system of claim 1, wherein the sheath slot is sized such that the sheath frictionally engages the suture in the deployed configuration.

8. The medical system of claim 1, wherein the sheath slot is sized such that the sheath does not frictionally engage the suture in the deployed configuration.

9. The medical device of claim 1, wherein the proximal end of the sheath slot terminates at a solid portion of the sheath.

10. A medical system comprising:
    at least one tissue anchor, the tissue anchor having an anchoring member connected to a suture;
    a needle having a length and a needle lumen sized to slidably receive the tissue anchor, the needle and needle lumen defining a longitudinal axis, a distal end of the needle defining a needle slot size to receive the suture therein;
    a flexible sheath having a sheath lumen sized to slidably receive the needle, the sheath extending along the length of the needle, a distal end of the sheath defining a sheath slot sized to receive the suture therein, wherein the needle slot and sheath slot are circumferentially mis-aligned;
    the system having a delivery configuration wherein the anchoring member is within the needle lumen and free ends of the suture extend from the anchoring member through the sheath slot such that the tissue anchor is retained within the needle lumen, wherein the sheath slot has proximal and distal portions each having a width greater than the width of the suture, and wherein the sheath includes one or more projections dividing the sheath slot into its proximal and distal portions to define a throat of the sheath slot having a reduced width, the throat dividing the sheath slot into a proximal slot portion and a distal slot portion, wherein the suture is mechanically retained within the proximal slot portion.

11. The medical system of claim 10, further comprising a plurality of tissue anchors each having an anchoring member connected to a suture, and wherein the plurality of tissue anchors are serially aligned within the needle lumen, and further comprising a pusher slidably received within the needle lumen, the pusher sized and positioned to engage the plurality of tissue anchors.

12. The medical system of claim 10, wherein the sheath slot extends through the distal end of the sheath.

* * * * *